US00PP22326P2

(12) United States Plant Patent
Wezelenburg

(10) Patent No.: US PP22,326 P2
(45) Date of Patent: Dec. 13, 2011

(54) ***VIBURNUM* PLANT NAMED 'JWW1'**

(50) Latin Name: *Viburnum plicatum*
Varietal Denomination: JWW1

(76) Inventor: Jan-Willem Wezelenburg, Hazerswoude-Dorp (NL)

( * ) Notice: Subject to any disclaimer, the term of this patent is extended or adjusted under 35 U.S.C. 154(b) by 0 days.

(21) Appl. No.: 12/925,593

(22) Filed: Oct. 25, 2010

(51) Int. Cl.
*A01H 5/00* (2006.01)
(52) U.S. Cl. ..... Plt./226
(58) Field of Classification Search ..... Plt./226
See application file for complete search history.

*Primary Examiner* — Kent L Bell
(74) *Attorney, Agent, or Firm* — C. A. Whealy

(57) ABSTRACT

A new and distinct cultivar of *Viburnum* plant named 'JWW1', characterized by its narrowly upright plant habit; vigorous growth habit; freely branching habit; numerous white-colored flowers; and good garden performance.

2 Drawing Sheets

Botanical designation: *Viburnum plicatum.*
Cultivar denomination: 'JWW1'.

BACKGROUND OF THE INVENTION

The present invention relates to a new and distinct cultivar of *Viburnum* plant, botanically known as *Viburnum plicatum* and hereinafter referred to by the name 'JWW1'.

The new *Viburnum* plant originated from an open-pollination in 2002 of *Viburnum plicatum* 'Pink Beauty', not patented, as the female, or seed, parent with an unknown selection of *Viburnum plicatum* as the male, or pollen, parent. The new *Viburnum* plant was discovered and selected by the Inventor in 2005 as a single flowering plant within the progeny of the stated open-pollination in a controlled environment in Hazerswoude-Dorp, The Netherlands.

Asexual reproduction of the new *Viburnum* plant by softwood cuttings in a controlled environment in Hazerswoude-Dorp, The Netherlands since 2006 has shown that the unique features of this new *Viburnum* plant are stable and reproduced true to type in successive generations of asexual reproduction.

SUMMARY OF THE INVENTION

Plants of the new *Viburnum* have not been observed under all possible environmental conditions. The phenotype may vary somewhat with variations in environment such as temperature and light intensity without, however, any variance in genotype.

The following traits have been repeatedly observed and are determined to be the unique characteristics of 'JWW1'. These characteristics in combination distinguish 'JWW1' as a new and distinct cultivar of *Viburnum* plant:

1. Narrowly upright plant habit.
2. Vigorous growth habit.
3. Freely branching habit.
4. Numerous white-colored flowers.
5. Good garden performance.

Plants of the new *Viburnum* can be compared to plants of the female parent, 'Pink Beauty'. Plants of the new *Viburnum* differ from plants of 'Pink Beauty' in the following characteristics:

1. Plants of the new *Viburnum* are more upright than and not as spreading as plants of 'Pink Beauty'.
2. Plants of the new *Viburnum* are more vigorous than plants of 'Pink Beauty'.
3. Plants of the new *Viburnum* and 'Pink Beauty' differ in flower color as plants of 'Pink Beauty' have pink-colored flowers.

Plants of the new *Viburnum* can be compared to plants of the *Viburnum plicatum* 'Watanabe', not patented. In side-by-side comparisons, plants of the new *Viburnum* differ from plants of 'Watanabe' in the following characteristics:

1. Plants of the new *Viburnum* are more vigorous than plants of 'Watanabe'.
2. Plants of the new *Viburnum* root faster and easier than plants of 'Watanabe'.

BRIEF DESCRIPTION OF THE PHOTOGRAPHS

The accompanying colored photographs illustrate the overall appearance of the new *Viburnum* plant showing the colors as true as it is reasonably possible to obtain in colored reproductions of this type. Colors in the photographs may differ slightly from the color values cited in the detailed botanical description which accurately describe the colors of the new *Viburnum* plant.

The photograph on the first sheet is a side perspective view of a typical plant of 'JWW1' grown in a container.

The photograph at the top of the second sheet is a close-up view of a typical inflorescence of 'JWW1'.

The photograph at the bottom of the second sheet is a close-up view of a typical leaf of 'JWW1'.

DETAILED BOTANICAL DESCRIPTION

The aforementioned photographs and following observations, measurements and values describe plants of the new *Viburnum* grown during the spring in 19-cm containers in a cold frame in Hazerswoude-Dorp, The Netherlands and under conditions which closely approximate commercial *Viburnum* production. During the production of the plants, day temperatures ranged from 15° C. to 25° C. and night temperatures ranged from 4° C. to 14° C. Plants were 18 months old when the photographs and the description were taken. In the description, color references are made to The Royal Horticultural Society Colour Chart, 2007 Edition, except where general terms of ordinary dictionary significance are used.

Botanical classification: *Viburnum plicatum* 'JWW1'.

Parentage:

*Female, or seed, parent.*—*Viburnum plicatum* 'Pink Beauty', not patented.

*Male, or pollen, parent.*—Unknown selection of *Viburnum plicatum,* not patented.

Propagation:

*Type.*—By softwood cuttings.

*Time to initiate roots.*—About one month at 20° C.

*Time to produce a rooted young plant.*—About five months at 18° C.

*Root description.*—Medium in thickness, slightly fleshy; close to 164A and N167A in color.

*Rooting habit.*—Moderate branching; medium density.

Plant description:

*Plant form and growth habit.*—Evergreen perennial shrub; narrowly upright plant habit; vigorous growth habit.

*Branching habit.*—Freely branching habit with about 16 primary lateral branches; pinching (removal of terminal apices) will enhance lateral branch development.

*Plant height.*—About 63 cm.

*Plant diameter* (*area of spread*).—About 43.9 cm.

Lateral branch description:

*Length.*—About 13 cm.

*Diameter.*—About 2.5 mm.

*Internode length.*—About 4.3 cm.

*Texture, developing.*—Densely pubescent.

*Texture, developed.*—Smooth, glabrous.

*Strength.*—Moderately strong.

*Color, developing.*—Upper surface, close to 177B to 177C; lower surface, close to 138B.

*Color, developed.*—Close to 199B to 199C.

Foliage description:

*Arrangement.*—Opposite, simple.

*Length.*—About 10.2 cm.

*Width.*—About 4.3 cm.

*Shape.*—Ovate to elliptic.

*Apex.*—Apiculate.

*Base.*—Rounded.

*Margin.*—Serrate.

*Texture, upper surface.*—Smooth, glabrous.

*Texture, lower surface.*—Moderately pubescent.

*Venation pattern.*—Pinnate.

*Color.*—Developing leaves, upper surface: Close to 143A. Developing leaves, lower surface: Between 137D and 143A. Fully expanded leaves, upper surface: Close to 137A and N137B; venation, close to 144B to 144C. Fully expanded leaves, lower surface: Close to 147B; venation, close to 144D.

*Petiole.*—Length: About 2.2 cm. Diameter: About 2 mm. Texture, upper and lower surfaces: Smooth, glabrous. Color, upper surface: Close to 183B to 183C. Color, lower surface: Close to 152A to 152C.

Flower description:

*Flower appearance/arrangement.*—Single rotate flowers arranged in terminal and axillary compound corymbs; freely flowering habit with usually about ten sterile flowers and about 36 fertile flowers per inflorescence; flowers face mostly upright.

*Natural flowering season.*—Continuous flowering from mid-May to October in The Netherlands; flowers begin flowering about six months after planting.

*Flower longevity.*—About ten days on the plant; flowers not persistent.

*Fragrance.*—None detected.

*Inflorescence height.*—About 7.5 cm.

*Inflorescence diameter.*—About 9.2 cm.

*Flower diameter, sterile flowers.*—About 3.8 mm.

*Flower depth* (*height*), *sterile flowers.*—About 7 mm.

*Flower diameter, fertile flowers.*—About 7 mm.

*Flower depth* (*height*), *fertile flowers.*—About 7 mm.

*Flower buds, sterile and fertile flowers.*—Length: About 2 mm. Diameter: About 2 mm. Shape: Globular. Color: Close to 155A.

*Petals, sterile flowers.*—Quantity per flower: Single whorl of five. Length: About 2 cm. Width: About 1.3 cm. Shape: Elliptic to irregularly obovate. Apex: Obtuse. Base: Fused. Margin: Entire. Texture, upper and lower surfaces: Smooth, glabrous. Color: When opening, upper surface: Close to 157D. When opening, lower surface: Close to NN155B. Fully opened, upper and lower surfaces: Close to NN155B to NN155C.

*Petals, fertile flowers.*—Quantity per flower: Single whorl of five. Length: About 4 mm. Width: About 2.5 mm. Shape: Broadly elliptic; convex. Apex: Broadly acute. Base: Fused. Margin: Entire, revolute. Texture, upper and lower surfaces: Smooth, glabrous. Color: When opening, upper surface: Close to 157D. When opening, lower surface: Close to NN155B. Fully opened, upper surface: Close to 157D. Fully opened, lower surface: Close to NN155B.

*Sepals, sterile flowers.*—Quantity per flower: Single whorl of five. Length: About 1 mm. Width: About 1 mm. Shape: Ovate. Apex: Acute. Base: Cuneate. Margin: Entire. Texture, upper and lower surfaces: Smooth, glabrous. Color: When opening and fully opened, upper surface: Close to 150C. When opening and fully opened, lower surface: Close to 145C.

*Sepals, fertile flowers.*—Quantity per flower: Single whorl of five. Length: About 1 mm. Width: About 0.6 mm. Shape: Ovate. Apex: Acute. Base: Cuneate. Margin: Entire. Texture, upper and lower surfaces: Smooth, glabrous. Color: When opening and fully opened, upper surface: Close to 150C. When opening and fully opened, lower surface: Close to 145C.

*Peduncles.*—Length: About 6.8 cm. Diameter: About 1.5 mm. Strength: Moderately strong. Texture: Smooth, glabrous. Color: Close to 145A.

*Pedicels, sterile flowers.*—Length: About 7 mm. Diameter: About 1 mm. Strength: Moderately strong. Texture: Smooth, glabrous. Color: Close to 145A.

*Pedicels, fertile flowers.*—Length: About 2 mm. Diameter: About 1 mm. Strength: Moderately strong. Texture: Smooth, glabrous. Color: Close to 145A.

*Reproductive organs, fertile flowers only.*—Androecium: Quantity per flower: About five. Filament length: About 5 mm. Filament color: Close to 157D. Anther shape: Flattened orbicular. Anther length: About 1 mm. Anther color: Close to 4C to 4D. Amount of pollen: Moderate. Pollen color: Close to 4B. Gynoecium: Quantity per flower: One. Pistil length: About 1.5 mm. Style length: About 0.5 mm. Style color: Close to 157C to 157D. Stigma shape:

Club-shaped, three-parted. Stigma color: Close to NN155B. Ovary color: Close to 145B to 145C.

*Seeds/fruits.*—Seed and fruit development have not been observed on plants of the new *Viburnum.*

Garden performance: Plants of the new *Viburnum* have been observed to have good garden performance and to tolerate rain and wind. Plants of the new *Viburnum* have been observed to be tolerant to USDA Hardiness Zone 5 and to high temperatures of about 30° C.

Pathogen/pest resistance: Plants of the new *Viburnum* have not been observed to be resistant to pathogens and pests common to *Viburnum.*

It is claimed:

1. A new and distinct *Viburnum* plant named 'JWW1' as illustrated and described.

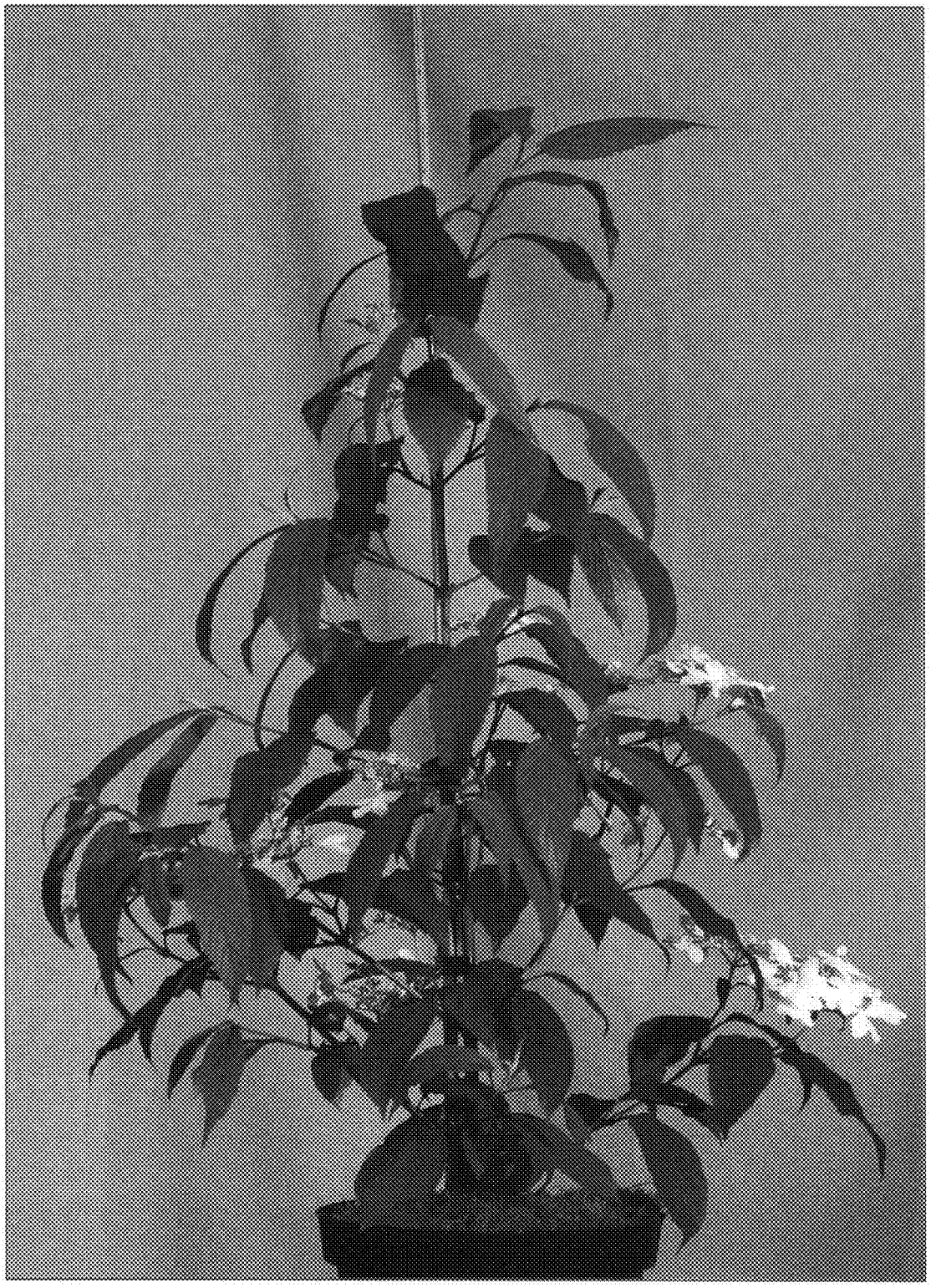

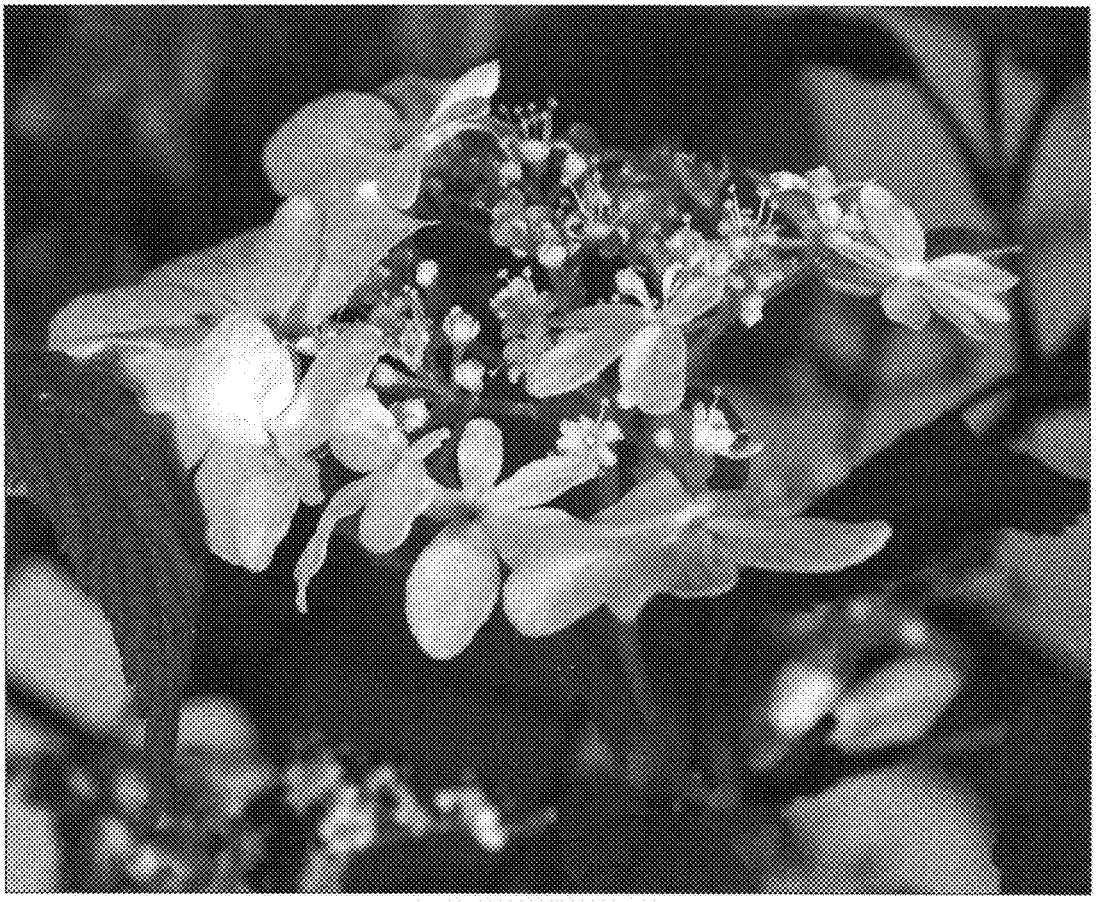
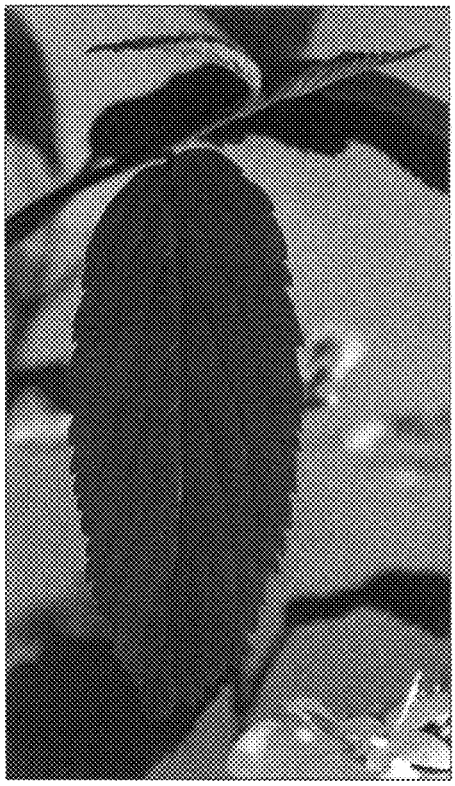

* * * * *